United States Patent [19]
White et al.

[11] Patent Number: 6,106,540
[45] Date of Patent: Aug. 22, 2000

[54] DILATOR AND INTRODUCER ASSEMBLY

[75] Inventors: Geoffrey H. White, East Balmain; Weiyun Yu, Five Dock, both of Australia

[73] Assignee: Baxter International Inc., Deerfield, Ill.

[21] Appl. No.: 09/117,129

[22] PCT Filed: Jan. 22, 1997

[86] PCT No.: PCT/AU97/00036

§ 371 Date: Jan. 13, 1999

§ 102(e) Date: Jan. 13, 1999

[87] PCT Pub. No.: WO97/26938

PCT Pub. Date: Jul. 31, 1997

[30] Foreign Application Priority Data

Jan. 22, 1996 [AU] Australia ................... PN7662

[51] Int. Cl.[7] .................................................. A61M 29/00
[52] U.S. Cl. ............................................ 606/191; 606/185
[58] Field of Search .................................... 606/190, 191, 606/192, 185

[56] References Cited

U.S. PATENT DOCUMENTS 5,254,107  10/1993  Soltesz ..................................... 604/282
5,569,218  10/1996  Berg .

FOREIGN PATENT DOCUMENTS

| 232994 | 8/1987 | European Pat. Off. . |
| 742029 | 11/1996 | European Pat. Off. . |
| 8-112355A | 5/1996 | Japan . |
| WO 87/07493 | 12/1987 | WIPO . |
| WO 92/15356 | 9/1992 | WIPO ........................... A61M 25/00 |
| WO 93/02735 | 2/1993 | WIPO . |
| WO 94/26336 | 11/1994 | WIPO . |

*Primary Examiner*—Michael Buiz
*Assistant Examiner*—Jonathan D. Goldberg
*Attorney, Agent, or Firm*—BHC, Vasc. Sys. Div.; Peter Jon Gluck; B. M. Canter

[57] ABSTRACT

A resiliently flexible body vessel or body cavity dilator that tapers toward one end and a transition zone that decreases in flexibility along the dilator away from the one end. The dilator can comprise a dilator arranged to be slid over a guidewire for use in the placement of an intraluminal graft bridging an aortic aneurysm. The dilator can also comprise an inner core of relatively stiff material surrounded by an outer layer of resiliently flexible material.

7 Claims, 5 Drawing Sheets

DILATOR AND INTRODUCER ASSEMBLY

FIELD OF THE INVENTION

The present invention relates to a body vessel or cavity dilator and to an introducer assembly for dilating a vessel or cavity and introducing a sheath therein.

BACKGROUND ART

There are many applications where it is necessary to insert a sheath or catheter into a body cavity or vessel. One means of facilitating the insertion of a sheath is to use a dilator fitted with a sheath that moves into the cavity or vessel and is then withdrawn leaving the sheath in place.

The placement of prosthetic devices, such as stents and grafts, intraluminally and the conduct of minimally invasive operative procedures has grown dramatically in recent years. Where, for example, an intraluminal graft is adapted for insertion into a patient to achieve bridging and occlusion of an aortic aneurysm, a sheath of sufficient diameter and adapted to assist with the delivery of the prosthetic device needs to be inserted into and through the femoral and associated iliac artery.

In many persons, the femoral artery, in passing over the pelvis, takes a quite tortuous path that can impede the passage of a catheter of sufficient width and stiffness and in turn also impede the travel of a graft through the catheter.

The present invention is directed to a device that alleviates the problem posed by such tortuous vessels.

STATEMENT OF INVENTION

According to a first aspect, the present invention comprises a resiliently flexible dilator for a bodily vessel, the dilator tapering towards one end to facilitate insertion of the dilator into the vessel and having a transition zone having a first end proximate the said one end and a second end distal the said one end, the physical properties of the dilator in the transition zone being such that the flexibility of the dilator at the second end of the transition zone is less than the flexibility of the dilator at the first end of the transition zone.

In one embodiment, the transition zone of the dilator comprises no more than half the length of the dilator, and more preferably no more than a quarter the length of the dilator. The resilient flexibility of the remainder of the dilator, apart from the transition zone, is preferably substantially constant along its length.

The dilator can taper along its whole length or just a portion adjacent the said one end. The tapering portion of the dilator towards one end can comprise a frusto-conical portion or hemispherical portion adjacent the said one end. The transition zone of the dilator can further overlap or be separate from the tapering portion of the dilator.

In one embodiment, the dilator is comprised of a polymeric or elastomeric material. The change in flexibility in the transition zone can be provided by an increase in cross-linking of the polymeric or elastomeric material along the dilator.

In another embodiment, the transition zone comprises an inner relatively stiff core of material having a tapered portion, with at least the tapered portion being surrounded by an outer layer of relatively resiliently flexible material that extends beyond the tapering portion of the core material so that the dilator undergoes a gradual decrease in flexibility in the region of the tapering portion of the core. In this embodiment, the dilator adjacent the said one end of the dilator can be formed from the relatively resiliently flexible material. This embodiment of the dilator can be fabricated by a co-extrusion of the inner core and the outer layer. The core can be fabricated from a 90/10 high density polypropylene and the outer layer from an ethylene-vinyl acetate (EVA) copolymer. Both the core and outer layer call include a barium sulfate component (eg: approximately 10%) to make the same radiopaque.

In a preferred embodiment, the dilator has a longitudinally extending axial bore to receive a guidewire already inserted through a vessel, and has a sheath disposed thereabout so that when the dilator is withdrawn the sheath is left in place in the vessel.

The flexibility of the said one end of the dilator is preferably substantially similar to the flexibility of the guidewire inserted through the dilator. The flexibility of the transition zone preferably gradually decreases from the first end to the second end of the transition zone until the flexibility is substantially similar to the flexibility of the associated sheath.

In a preferred embodiment, the dilator is arranged so as to be inserted into the femoral and associated iliac artery so as to allow the placement of a sheath through these arteries for use in the intraluminal placement of an intraluminal graft bridging an aortic aneurysm. The guidewire in this embodiment is preferably an Amplatz extra stiff (AES) guidewire of 0.035" diameter.

According to a second aspect, the present invention consists in an introducer assembly for introducing a sheath into a bodily vessel comprising a guidewire, a resiliently flexible dilator tapering towards one end and a longitudinally extending axial bore that can receive the guidewire, and a sheath positioned around the dilator, the dilator having a transition zone having a first end proximate the said one end and a second end distal the said one end, the physical properties of the dilator in the transition zone being such that the flexibility of the dilator at the second end of the transition zone is less than the flexibility of the dilator at the first end of the transition zone.

Preferably, the said one end of the dilator has a flexibility substantially similar to that of the guidewire. The flexibility of the transition zone preferably gradually decreases from its first end to its second end, the second end having a flexibility substantially similar to the flexibility of the associated sheath.

BRIEF DESCRIPTION OF THE DRAWINGS

Hereinafter by way of example only, preferred embodiments of the invention are described with reference to the accompanying drawings, in which.

PREFERRED MODE OF CARRYING OUT THE INVENTION

Figure 1:
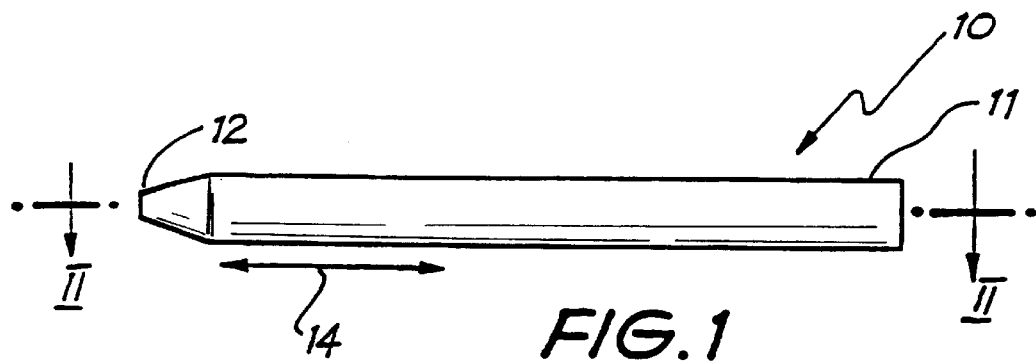
FIG. 1 is a side elevational view of a dilator according to the present invention.
Figure 2:
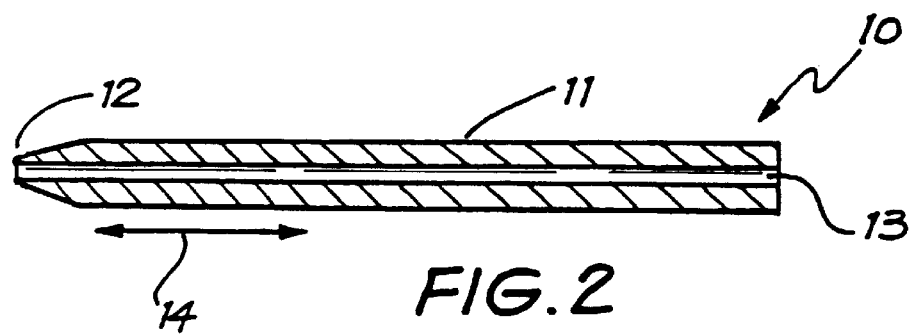
FIG. 2 is a longitudinal cross-sectional view along line II—II of the dilator of FIG. 1.

A resiliently flexible dilator for a vessel according to the present invention is generally depicted as 10 in FIGS. 1 and 2. The dilator 10 comprises a substantially cylindrical shaft 11 and a tapering portion adjacent the end 12 and a longitudinally extending axial bore 13.

In the embodiment depicted in FIGS. 1 and 2, the dilator 10 is fabricated from a elastomeric material. In a transition zone (depicted generally as 14) proximate the end 12, the cross-linking of the elastomeric material increases away from the end 12 so leading to a decrease in the flexibility of the elastomeric material in the region 14 away from the end 12. The resilient flexibility of the remainder of the dilator 10 is substantially constant.

Figure 4:
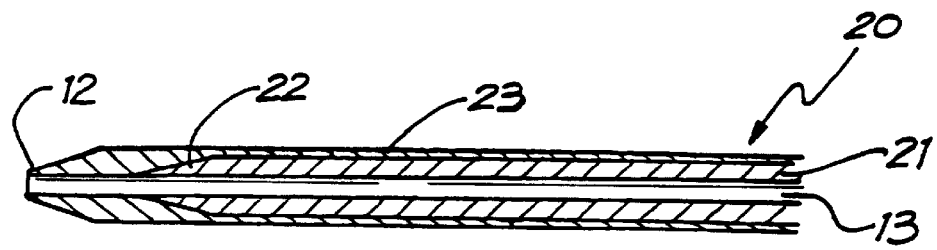
FIG. 4 is a longitudinal cross-sectional view of another embodiment of a dilator according to the present invention.

In the embodiment of the dilator depicted generally as 20 in FIG. 4, the dilator 20 comprises a relatively stiff core 21 of 90/10 high density polypropylene, having a tapering portion 22, surrounded by a relatively resiliently flexible EVA copolymer outer layer 23 that extends beyond the tapering portion 22 of the core 21 and is used to form the dilator adjacent the end 12. The tapering portion 22 of the core 21 results in a gradual decrease in flexibility of the dilator 20 in the region of this taper 22 between the end 12 and the remainder of the dilator 20. Both the core 21 and the outer layer 23 include a barium sulfate component of about 10% to make them radiopaque. Those of ordinary skill in the art will recognise that materials possessing similar characteristics to those previously described may alternatively be used to fabricate the core 21 and outer layer 23.

Figure 3:
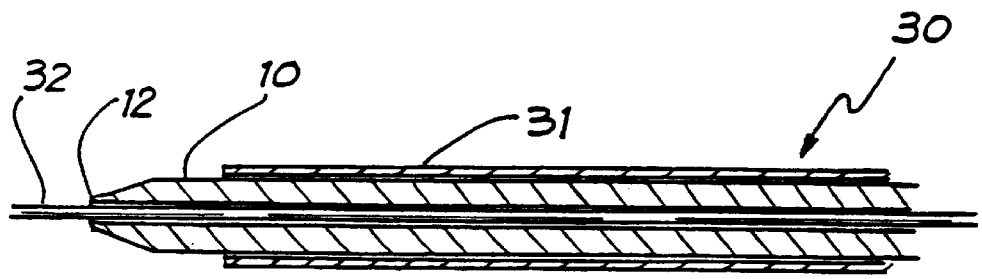
FIG. 3 is a longitudinal cross-sectional view of the dilator of FIG. 1 ready for insertion into a body vessel or cavity over a guidewire.

The dilator 10 or 20 can form part of a sheath introducer assembly generally depicted as 30 in FIG. 3. The introducer assembly 30 is adapted to place a sheath 31 through and within a tortuous blood vessel. The assembly 30 comprises a guidewire 32 that passes through the bore 13 of the dilator, and the sheath 31.

An example of an application where a dilator and an introducer assembly according to the present invention are specially beneficial is in the placement of intraluminal grafts into a patient to achieve bridging and occlusion of an aortic aneurysm.

Figure 5:
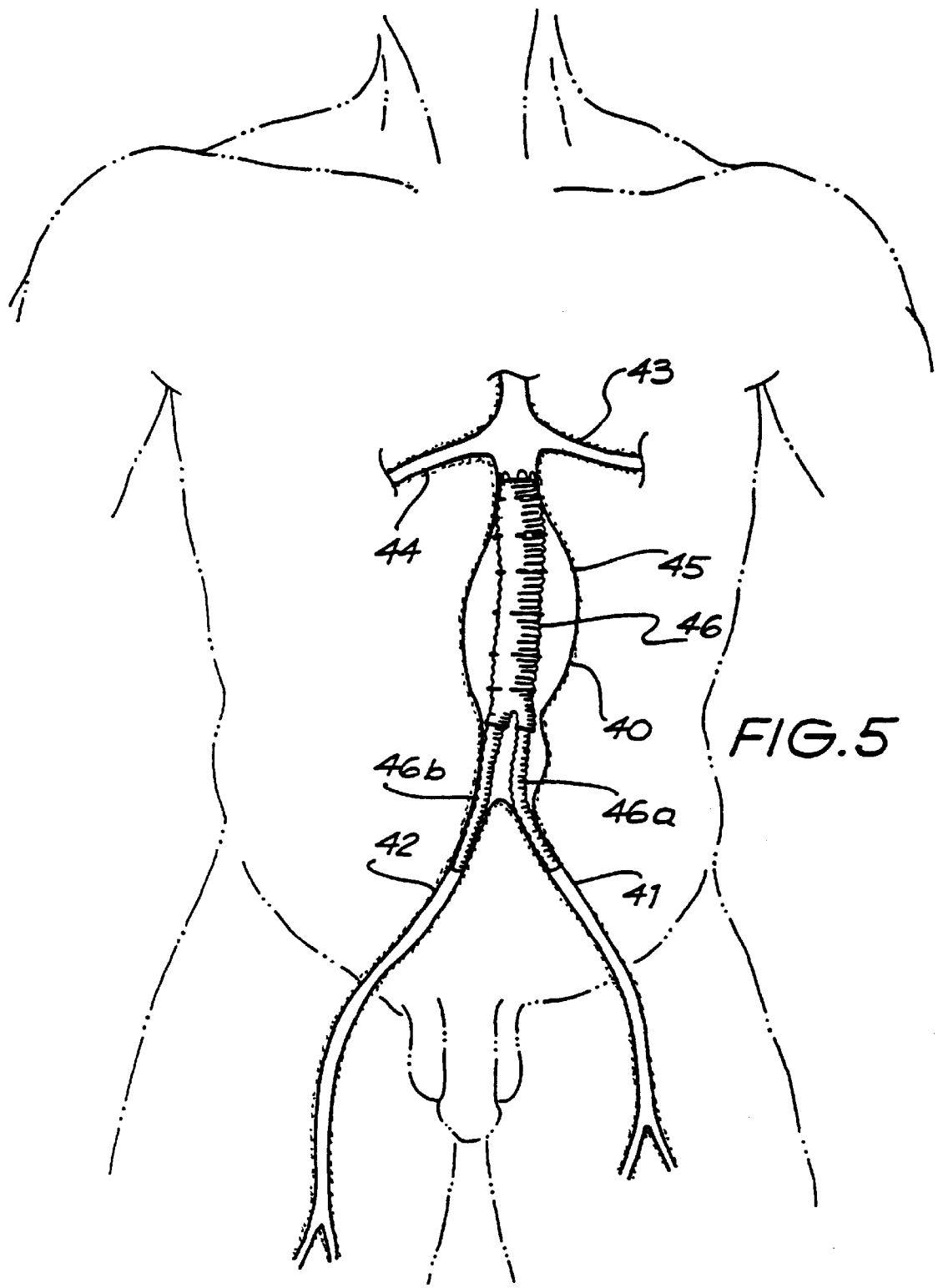
FIG. 5 is a diagrammatic representation of a ventral view of a patient having all aortic aneurysm bridged by a trouser graft.

As is seen in FIG. 5, the aorta 40 is connected to the left and right iliac arteries 41 and 42. In FIG. 5, the aortic aneurysm 45 is located between the renal arteries 43 and 44 and extends down the left iliac artery 41. One means of bridging the aneurysm 45 is to use a trouser graft 46 that is provided with a bifurcation to form a pair of short tubular extensions 46a and 46b that extend down the iliac arteries 41 and 42 respectively.

Figure 6A:
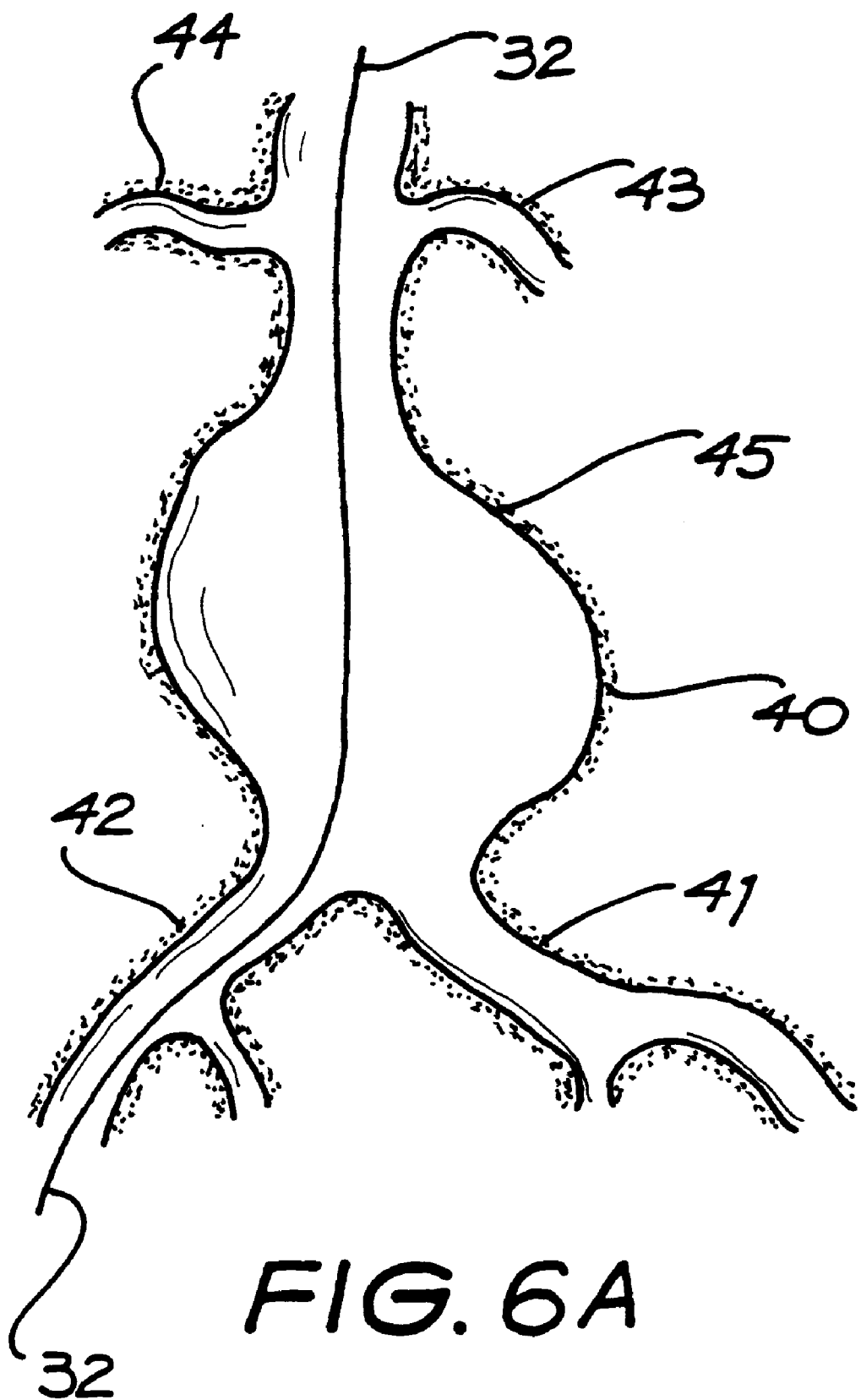
FIGS. 6A–6C show stages of using a dilator according to the present invention to insert a sheath into and along a femoral artery, being the initial steps in inserting a trouser graft intraluminally into a patient having an aortic aneurysm.

The method for positioning a sheath 31 into each of the iliac arteries 41 and 42, being one of the steps necessary to successfully place the intraluminal graft 46 in position within the aorta 40 will now be described with reference to FIGS. 6A–6C. In carrying out the method an incision is made to expose one of the femoral arteries (ipsilateral), which flows from the corresponding iliac artery, and using the Seldinger needle technique, a 0.035" diameter floppy tipped flexible guidewire is inserted into and through the femoral artery and then the iliac artery 42 into the aorta 40 such that it transverses the aneurysm 45. An 8 French haemostatic sheath is then introduced over the guidewire to control bleeding. An angiographic catheter is introduced to allow an angiogram to be taken of the patient to shown the position of the renal arteries 43, 44 and other relevant anatomical structures of the patient.

An Amplatz extra stiff (AES) guidewire 32 (0.035" diameter) is then passed through the angiographic catheter into the aorta 40. After withdrawal of the angiographic catheter, the stiff guidewire 32 is left in situ (see FIG. 6A).

Figure 6B:
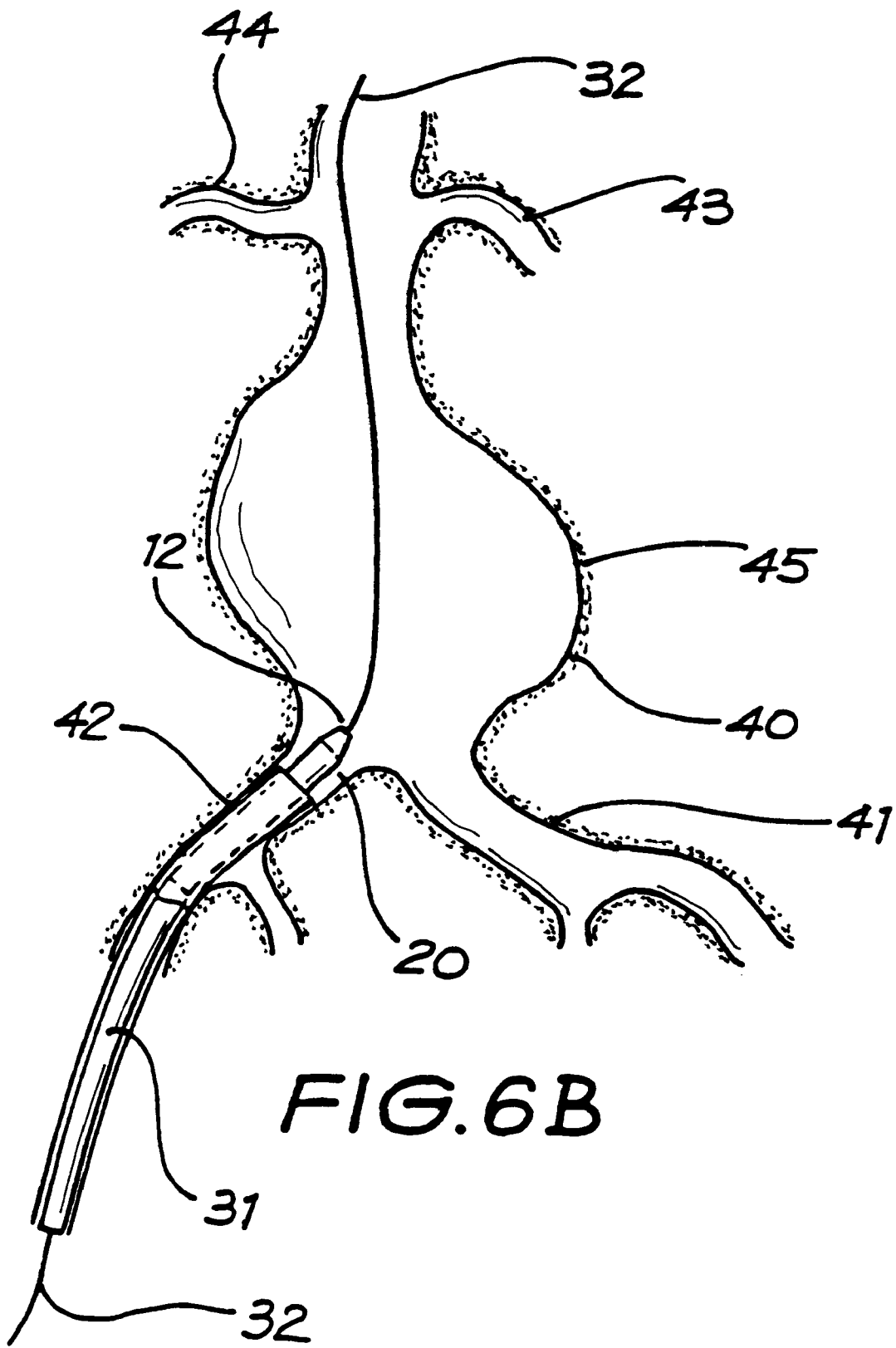

A resiliently flexible dilator 20 (as depicted in FIG. 4), with sheath 31, preferably of 24 French, is then introduced into the femoral artery and along the ipsilateral iliac artery 42 (see FIG. 6B). The tapering of the dilator towards the end 12 allows the dilator to follow the guidewire 32 through the tortuous portion of the femoral and iliac artery before entering the aorta 40. The gradual decrease in flexibility provided by the tapering portion 22 of the dilator core 21 facilitates insertion of the dilator 20.

Figure 6C:
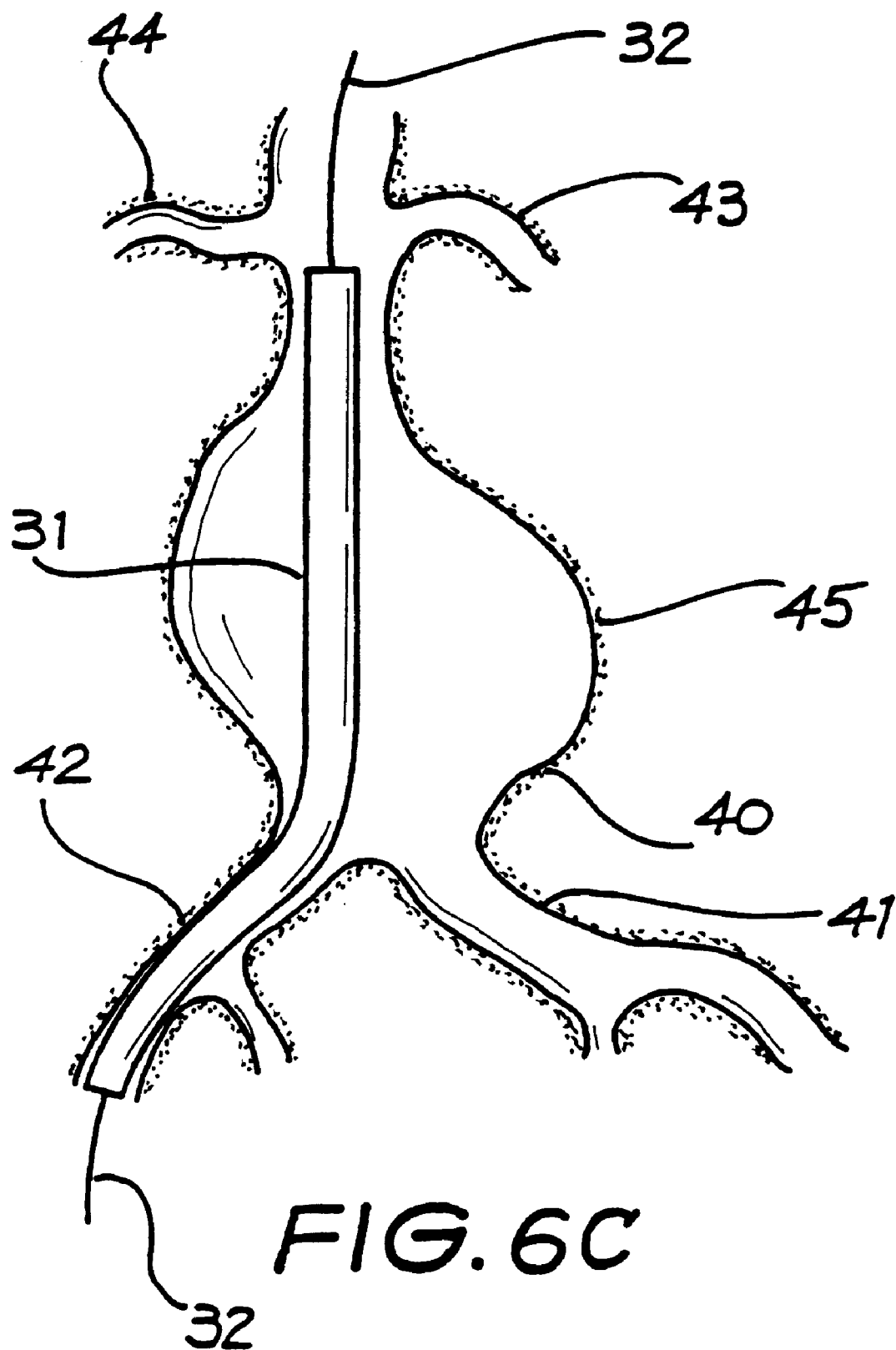

The dilator 20 is pushed through the aorta 40 to proximate the renal arteries 43,44 and then withdrawn leaving the sheath 31 extending across the aorta 40 as depicted in FIG. 6C.

With the sheath 31 in place, a pre-packaged graft 46 can be passed through the sheath and appropriately placed in the aorta 40, as is depicted in FIG. 5.

It will be appreciated by persons skilled in the art that numerous variations and/or modifications may be made to the invention as shown in the specific embodiments without departing front the spirit or scope of the invention as broadly described. The present embodiments are, therefore, to be considered in all respects as illustrative and not restrictive.

What is claimed is:

1. A resiliently flexible dilator for a bodily vessel, the dilator tapering towards one end to facilitate insertion of the dilator into the vessel and having a transition zone having a first end proximate the said one end and a second end distal the said one end, the physical properties of the dilator in the transition zone being such that the flexibility of the dilator at the second end of the transition zone is less than the flexibility of the dilator at the first end of the transition zone;

wherein the transition zone of the dilator comprises at least one of no more than half the length of the dilator, and no more than one quarter of the length of the dilator;

wherein the flexibility of the transition zone is gradually decreasing between its first and its second end and wherein the flexibility of the dilator apart from the transition zone has a substantially constant flexibility and further comprises an elastomeric material; and, wherein the change in flexibility of the transition zone of the dilator is provided by an increase in cross-linking of the elastomeric material comprising the transition zone away from its first end.

2. A resiliently flexible dilator for a bodily vessel, the dilator tapering towards one end to facilitate insertion of the dilator into the vessel and having a transition zone having a first end proximate the said one end and a second end distal the said one end, the physical properties of the dilator in the transition zone being such that the flexibility of the dilator at the second end of the transition zone is less than the flexibility of the dilator at the first end of the transition zone;

wherein the transition zone of the dilator comprises at least one of no more than half the length of the dilator, and no more than one quarter of the length of the dilator;

wherein the flexibility of the transition zone is gradually decreasing between its first and its second end and wherein the flexibility of the dilator apart from the transition zone has a substantially constant flexibility and further comprises an elastomeric material;

wherein the change in flexibility of the transition zone of the dilator is provided by an increase in cross-linking of the elastomeric material comprising the transition zone away from its first end;

wherein the transition zone comprises an inner relatively stiff core of material having a tapering portion with at least the tapering portion being surrounded by a relatively resiliently flexible outer layer that extends beyond the tapering portion of the core material;

wherein the inner core is fabricated from high density polypropylene, and the outer layer is fabricated from an EVA copolymer.

3. A resiliently flexible dilator for a bodily vessel, the dilator tapering towards one end to facilitate insertion of the dilator into the vessel and having a transition zone having a first end proximate the said one end and a second end distal the said one end, the physical properties of the dilator in the transition zone being such that the flexibility of the dilator at the second end of the transition zone is less than the flexibility of the dilator at the first end of the transition zone;

wherein the transition zone of the dilator comprises at least one of no more than half the length of the dilator, and no more than one quarter of the length of the dilator;

wherein the flexibility of the transition zone is gradually decreasing between its first and its second end and wherein the flexibility of the dilator apart from the transition zone has a substantially constant flexibility and further comprises an elastomeric material;

wherein the change in flexibility of the transition zone of the dilator is provided by an increase in cross-linking of the elastomeric material comprising the transition zone away from its first end;

wherein the transition zone comprises an inner relatively stiff core of material having a tapering portion with at least the tapering portion being surrounded by a relatively resiliently flexible outer layer that extends beyond the tapering portion of the core material;

wherein the inner core is fabricated from high-density polypropylene;

the outer layer is fabricated from an EVA copolymer;

wherein the dilator has a longitudinally extending axial bore to receive a guidewire already inserted through the vessel, and has a sheath disposed thereabout so that when the dilator is withdrawn from the vessel the sheath is left in place in the vessel;

wherein the flexibility of the guidewire at said one end and the first end of the transition zone are substantially similar to the flexibility of the guidewire, and;

wherein the flexibility of the second end of the transition zone is substantially similar to the flexibility of the associated sheath.

4. An introducer assembly for introducing a sheath into a bodily vessel comprising a guidewire, a resiliently flexible dilator tapering towards one end of a longitudinally extending axial bore that can receive the guidewire, and a sheath positioned around the dilator, the dilator having a transition zone having a first end proximate the said one end and a second end distal the said one end, the physical properties of the dilator in the transition zone being such that the flexibility of the dilator at the second end of the transition zone is less than the flexibility of the dilator at the at the first end of the transition zone, and;

wherein the one end of the dilator has a flexibility substantially similar to the guidewire.

5. A medical dilator, comprising an elongate shaft that is flexible along its entire length from a proximal end to a distal end, the shaft having a substantially cylindrical outer surface from the proximal end to a tapered portion adjacent the distal end and an axial bore from a proximal end to the distal end, the shaft further including a transition zone having an axial length located adjacent the tapered portion, the transition zone exhibiting a gradual decrease in flexibility along its axial length in the proximal direction, the elongate shaft having a substantially constant flexibility proximal to the transition zone.

6. The dilator of claim 5, wherein the shaft is made of an elastomeric material, and wherein the gradual decrease in flexibility in the transition zone is provided by an increase in cross-linking of the elastomeric material in the proximal direction within the transition zone.

7. The dilator of claim 5, wherein the shaft comprises an inner core having a tapered distal end that terminates at an axial location adjacent the tapered portion of the shaft, and an outer layer surrounding the core along its length and extending beyond the tapered distal end of the core to define the tapered portion of the shaft, the outer layer being relatively more flexible than the inner core, and wherein the gradual decrease in flexibility in the transition zone is provided by the increasing cross-section of the core along its tapered distal end.

* * * * *

UNITED STATES PATENT AND TRADEMARK OFFICE
CERTIFICATE OF CORRECTION

PATENT NO. : 6,106,540
DATED : August 22, 2000
INVENTOR(S) : Geoffrey H. White, et al.

It is certified that error appears in the above-identified patent and that said Letters Patent is hereby corrected as shown below:

Title page,
Item [75] Inventors, should read --Mark Dehdashtian, Costa Mesa, Calif.; Geoffrey H. White, East Balmain and Weiyun Yu, Five Dock both of Australia--

Signed and Sealed this

Seventeenth Day of July, 2001

Attest:

NICHOLAS P. GODICI
Attesting Officer   Acting Director of the United States Patent and Trademark Office